US00PP21904P2

(12) United States Plant Patent
Lommerse

(10) Patent No.: US PP21,904 P2
(45) Date of Patent: May 3, 2011

(54) ***GAURA* PLANT NAMED 'SUMMER EMOTIONS'**

(50) Latin Name: *Gaura lindheimeri*
Varietal Denomination: Summer Emotions

(75) Inventor: Piet R. J. Lommerse, Noordwijkerhout (NL)

(73) Assignee: Compass Plants B.V., Hillegom (NL)

( * ) Notice: Subject to any disclaimer, the term of this patent is extended or adjusted under 35 U.S.C. 154(b) by 0 days.

(21) Appl. No.: 12/653,750

(22) Filed: Dec. 16, 2009

(51) Int. Cl.
*A01H 5/00* (2006.01)

(52) U.S. Cl. ..... Plt./432

(58) Field of Classification Search ..... Plt./432
See application file for complete search history.

(56) References Cited

U.S. PATENT DOCUMENTS

PP16,981 P2 * 8/2006 Lommerse ..... Plt./432

OTHER PUBLICATIONS

UPOV ROM GTITM Jouve Retrieval Database GTI Jouve Retrieval Software 2010/03 Citation for 'Summer Emotions.'*

* cited by examiner

*Primary Examiner* — Wendy Haas
(74) *Attorney, Agent, or Firm* — C. A. Whealy

(57) ABSTRACT

A new and distinct cultivar of *Gaura* plant named 'Summer Emotions', characterized by its upright and outwardly spreading growth habit; moderately vigorous growth habit; freely branching habit; freely flowering habit; long flowering period; pink-colored flowers; and good garden performance.

2 Drawing Sheets

Botanical designation: *Gaura lindheimeri.*
Cultivar denomination: 'SUMMER EMOTIONS'.

BACKGROUND OF THE INVENTION

The present invention relates to a new and distinct cultivar of *Gaura* plant, botanically known as *Gaura lindheimeri* and hereinafter referred to by the name 'Summer Emotions'.

The new *Gaura* plant is a naturally-occurring whole plant mutation of *Gaura lindheimeri* 'Gausudre', disclosed in U.S. Plant Pat. No. 16,981. The new *Gaura* plant was discovered and selected by the Inventor as a single flowering plant within a population of plants of 'Gausudre' in a controlled greenhouse environment in Noordwijkerhout, The Netherlands in July, 2007.

Asexual reproduction of the new *Gaura* plant by terminal cuttings in a controlled environment in Noordwijkerhout, The Netherlands since 2008, has shown that the unique features of this new *Gaura* plant are stable and reproduced true to type in successive generations.

SUMMARY OF THE INVENTION

Plants of the new *Gaura* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Summer Emotions'. These characteristics in combination distinguish 'Summer Emotions' as a new and distinct cultivar of *Gaura:*

1. Upright and outwardly spreading growth habit.
2. Moderately vigorous growth habit.
3. Freely branching habit.
4. Freely flowering habit.

5. Long flowering period.
6. Pink-colored flowers.
7. Good garden performance.

Plants of the new *Gaura* can be compared to plants of the parent, 'Gausudre'. Plants of the new *Gaura* differ from plants of 'Gausudre' in the following characteristics:

1. Leaves of plants of the new *Gaura* are dark green in color whereas leaves of plants of 'Gausudre' are dark green with reddish overtones.
2. Plants of the new *Gaura* and 'Gausudre' differ in flower color as plants of 'Gausudre' have deep rose-colored flowers.

Plants of the new *Gaura* can also be compared to plants of *Gaura lindheimeri* 'Siskiyou Pink', not patented. In side-by-side comparisons conducted in Noordwijkerhout, The Netherlands, plants of the new *Gaura* differed from plants of 'Siskiyou Pink' in the following characteristics:

1. Plants of the new *Gaura* were more compact than plants of 'Siskiyou Pink'.
2. Leaves of plants of the new *Gaura* were dark green in color whereas leaves of plants of 'Siskiyou Pink' were dark green with reddish overtones.
3. Plants of the new *Gaura* and 'Siskiyou Pink' differed in flower color.

BRIEF DESCRIPTION OF THE PHOTOGRAPHS

The accompanying colored photographs illustrate the overall appearance of the new *Gaura* plant, showing the colors as true as it is reasonably possible to obtain in colored reproductions of this type. Colors in the photographs may differ slightly from the color values cited in the detailed botanical description which accurately describe the colors of the new *Gaura* plant.

The photograph on the first sheet comprises a side perspective view of a typical plant of 'Summer Emotions' grown in a container.

The photograph at the top of the second sheet is a close-up view of typical flowers of 'Summer Emotions'.

The photograph at the bottom of the second sheet is a close-up view of typical leaves of 'Summer Emotions'.

DETAILED BOTANICAL DESCRIPTION

The aforementioned photographs and following observations, measurements and values describe plants grown in 17-cm containers in an outdoor nursery in Noordwijkerhout, The Netherlands during the summer and early autumn and under conditions which approximate commercial production. During the production of the plants, day temperatures ranged from 12° C. to 32° C. and night temperatures ranged from 6° C. to 18° C. Plants were two years old when the photographs and description were taken. In the following description, color references are made to The Royal Horticultural Society Colour Chart, 2007 Edition, except where general terms of ordinary dictionary significance are used.

Botanical classification: *Gaura lindheimeri* 'Summer Emotions'.

Parentage: Naturally-occurring whole plant mutation of *Gaura lindheimeri* 'Gausudre', disclosed in U.S. Plant Pat. No. 16,981.

Propagation:

*Type.*—By vegetative cuttings.

*Time to initiate roots.*—About three weeks at 20° C.

*Time to produce a rooted young plant.*—About six weeks at 20° C.

*Root description.*—Fine, fibrous.

*Rooting habit.*—Freely branching; dense.

Plant description:

*Plant and growth habit.*—Herbaceous perennial; compact, upright and outwardly spreading growth habit; broad inverted triangle; freely branching habit with about 22 lateral branches developing per plant, pinching enhances lateral branch development; dense and bushy plant form; moderately vigorous growth habit.

*Plant height.*—About 36.5 cm.

*Plant diameter.*—About 51.4 cm.

Lateral branch description:

*Length.*—About 13.5 cm.

*Diameter.*—About 2 mm.

*Internode length.*—About 1.6 cm.

*Strength.*—Strong.

*Aspect.*—Upright to outwardly arching.

*Texture.*—Pubescent.

*Color.*—Close to 138B.

Foliage description:

*Arrangement.*—Alternate; simple; sessile.

*Length.*—About 3.8 cm.

*Width.*—About 7 mm.

*Shape.*—Oblanceolate to narrowly elliptic.

*Apex.*—Acute.

*Base.*—Attenuate.

*Margin.*—Shallowly crenate.

*Texture, upper and lower surfaces.*—Pubescent.

*Venation pattern.*—Pinnate.

*Color.*—Developing leaves, upper surface: Close to 137B. Developing leaves, lower surface: Close to 137B to 137C. Fully expanded leaves, upper surface: Close to N137B; venation, close to 138B to 138C. Fully expanded leaves, lower surface: Close to N137A; venation, close to 138B to 138C.

Flower description:

*Flower arrangement and habit.*—Single flowers arranged on upright terminal and axillary racemes; freely flowering habit with about 8 or 15 flowers per terminal or axillary inflorescence respectively; flowers face upright to outwardly.

*Fragrance.*—None detected.

*Natural flowering season.*—Plants flower continuously from July to September in The Netherlands.

*Flower longevity.*—Individual flowers last about five days on the plant; flowers not persistent.

*Inflorescence height, terminal racemes.*—About 25.9 cm.

*Inflorescence diameter, terminal racemes.*—About 3.5 cm.

*Inflorescence height, axillary racemes.*—About 16.5 cm.

*Inflorescence diameter, axillary racemes.*—About 3.5 cm.

*Flower diameter.*—About 2.5 cm.

*Flower depth (height).*—About 3.2 cm.

*Flower bud.*—Length: About 1.6 cm. Diameter: About 2 mm. Shape: Narrowly oblong. Color: Close to 181A; towards the apex, close to 146B.

*Petals.*—Arrangement: Four in a single whorl. Length: About 1.6 cm. Width: About 8 mm. Shape: Obovate. Apex: Broadly acute. Base: Attenuate. Margin: Entire. Texture, upper and lower surfaces: Smooth, glabrous. Color: When opening, upper surface: Close to NN155B; towards the margins, close to 62B. When opening, lower surface: Close to NN155B; towards the margins, close to 62A. Fully opened, upper and lower surfaces: Close to 65A; towards the center, close to 69D; color becoming closer to 63A with development.

*Sepals.*—Arrangement: Three in a single whorl. Length: About 1.7 cm. Width: About 1 mm. Shape: Narrowly lanceolate. Apex: Narrowly acute. Base: Broadly cuneate. Margin: Entire. Texture, upper and lower surfaces: Smooth, glabrous. Color, immature, upper surface: Close to 181B; towards the apex, close to 146B. Color, immature, lower surface: Close to 181A; towards the apex, close to 146B. Color, mature, upper and lower surfaces: Close to 181A; towards the apex, close to 146B.

*Peduncles.*—Length, terminal racemes: About 24.8 cm. Length, axillary racemes: About 15.4 cm. Diameter: About 1 mm. Strength: Strong. Aspect: Erect to about 40° from vertical. Texture: Pubescent. Color: Close to 138B.

*Pedicels.*—Length: About 2 mm. Diameter: About 1 mm. Strength: Moderately strong. Aspect: About 35° from vertical. Texture: Pubescent. Color: Close to 146D.

*Reproductive organs.*—Stamens: Quantity: About eight per flower. Filament length: About 1 cm. Filament color: Close to N155C. Anther shape: Narrowly oblong. Anther length: About 4 mm. Anther color: Close to 183A. Pollen amount: Moderate. Pollen color: Close to 11B. Pistils: Quantity: One per flower. Pistil length: About 1.5 cm. Style length: About 1.3 cm. Style color: Close to 62B. Stigma shape: Four-parted, cleft. Stigma color: Close to 145C. Ovary color: Close to 178A to 178B. Seed/fruit: Seed and fruit development have not been observed on plants of the new *Gaura*.

Garden performance: Plants of the new *Gaura* have been observed to have good garden performance and tolerate wind, rain and temperatures ranging from about −5° C. to about 30° C.

Pathogen/pest resistance: Plants of the new *Gaura* have not been observed to be resistant to pathogens and pests common to *Gaura*.

It is claimed:

1. A new and distinct *Gaura* plant named 'Summer Emotions' as illustrated and described.

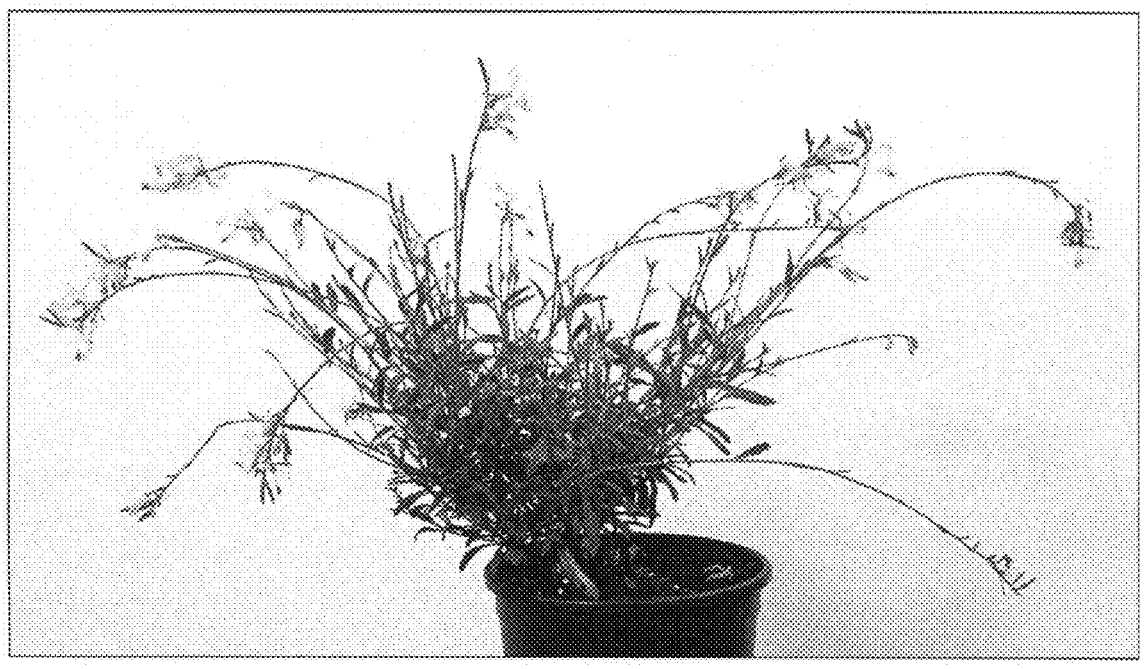

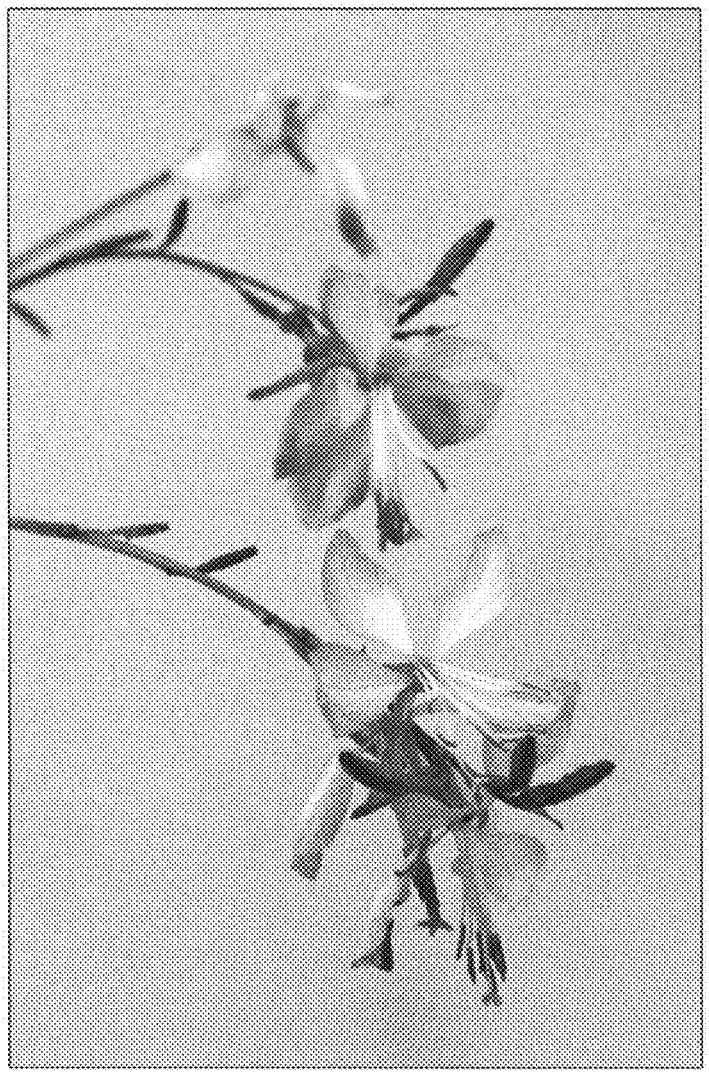
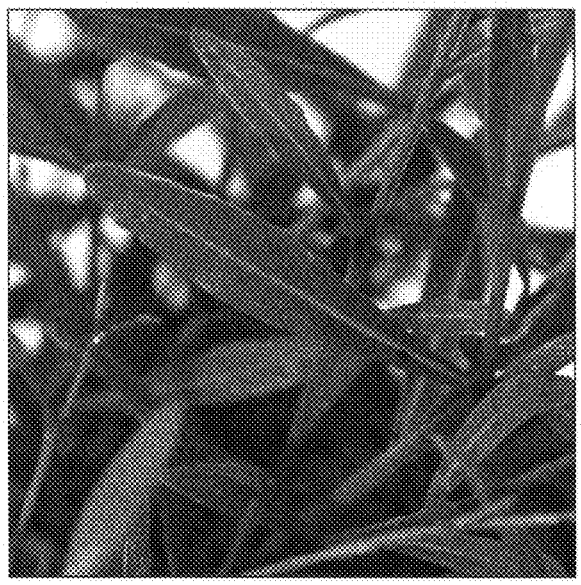

* * * * *